United States Patent
Schwan et al.

(10) Patent No.: US 10,434,201 B2
(45) Date of Patent: Oct. 8, 2019

(54) METHOD FOR CONTINUOUS VIRUS INACTIVATION

(71) Applicant: Bayer Aktiengesellschaft, Leverkusen (DE)

(72) Inventors: Peter Schwan, Leverkusen (DE); Andrea Vester, Duesseldorf (DE); Martin Lobedann, Cologne (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 6 days.

(21) Appl. No.: 15/569,635

(22) PCT Filed: Apr. 25, 2016

(86) PCT No.: PCT/EP2016/059169
§ 371 (c)(1),
(2) Date: Sep. 14, 2018

(87) PCT Pub. No.: WO2016/173982
PCT Pub. Date: Nov. 3, 2016

(65) Prior Publication Data
US 2019/0117803 A1    Apr. 25, 2019

(30) Foreign Application Priority Data
Apr. 28, 2015 (EP) .................... 15165505

(51) Int. Cl.
*A61L 2/04* (2006.01)
*A61L 2/00* (2006.01)
*A61L 2/10* (2006.01)

(52) U.S. Cl.
CPC .......... *A61L 2/0088* (2013.01); *A61L 2/0005* (2013.01); *A61L 2/04* (2013.01); *A61L 2/10* (2013.01); *A61L 2202/21* (2013.01)

(58) Field of Classification Search
CPC ............. A61L 2/0088; A61L 2/04; A61L 2/10
See application file for complete search history.

(56) References Cited

U.S. PATENT DOCUMENTS

| | | |
|---|---|---|
| 2002/0096648 A1 | 7/2002 | Kaiser et al. |
| 2004/0248076 A1 | 12/2004 | Kaiser et al. |
| 2009/0178495 A1 | 7/2009 | Steigmiller et al. |
| 2009/0269250 A1 | 10/2009 | Panagiotou et al. |

FOREIGN PATENT DOCUMENTS

| | | |
|---|---|---|
| EP | 1339643 B1 | 9/2003 |
| EP | 1464342 B1 | 10/2004 |
| EP | 1914202 A1 | 4/2008 |

(Continued)

OTHER PUBLICATIONS

PCT International Search Report for PCT/EP2016/059169, dated Jan. 6, 2016.

(Continued)

*Primary Examiner* — Sean E Conley
(74) *Attorney, Agent, or Firm* — McBee Moore Woodward & Vanik IP, LLC

(57) ABSTRACT

The invention provides a method for continuous virus inactivation. The product stream is segmented by introducing a separating medium which is immiscible with the product stream and the segmented product stream is transported into a reactor 1 as detention segment under virus-inactivating conditions for the required detention time.

10 Claims, 5 Drawing Sheets

(56) References Cited

FOREIGN PATENT DOCUMENTS

| EP | 1916224 A1 | 4/2008 |
| WO | 1998002237 A1 | 1/1998 |
| WO | 2002/038191 A2 | 5/2002 |
| WO | 2004103539 A2 | 12/2004 |
| WO | 2006039568 A1 | 4/2006 |
| WO | 2015/135844 A1 | 9/2015 |

OTHER PUBLICATIONS

Sofer, Gail, "Virus Inactivation in the 1990s—and into the 21st Century. Part 4, Culture Media, Biotechnology Products, and Vaccines", BioPharm International, Jan. 2003, pp. 50-57.
Roeseling, Dirk et al., Microreactor-Based Synthesis of Molecularly Imprinted Polymer Beads Used for Explosive Detection, Organic Process Research & Development, 2009, pp. 1007-1013, vol. 13.

Segmented flow with hydrophobic surfaces

Segmented flow with hydrophilic surfaces

Gas introduction via controlled valve

Gas introduction via controlled pump

US 10,434,201 B2

METHOD FOR CONTINUOUS VIRUS INACTIVATION

CROSS-REFERENCE TO RELATED APPLICATIONS

This application is a National Stage entry of International Application No. PCT/EP2016/059169, filed Apr. 25, 2016, which claims priority to European Patent Application No. 15165505.7, filed Apr. 28, 2015.

BACKGROUND

Field

The present invention relates to a method for continuous virus inactivation in a detention time segment.

Description of Related Art

Biopharmaceutical production processes require various orthogonal steps for virus reduction. A method frequently used for inactivating (coated) viruses is contact with an acid medium.

Virus inactivation at a low pH in the batch mode is known and frequently employed in biopharmaceutical production of active ingredients, e.g. antibodies (Sofer 2003, Virus Inactivation in the 1990s—and into the 21st Century. Part 4. BioPharm International). In this case, the material that is to be inactivated, and a liquid that potentially contains active viruses, are introduced into a suitable container, adjusted to a pH≤4 using an acidic solution, if necessary homogenized, and allowed to stand for the required time. Inactivation of the viruses takes place as a result of the contact of the viruses with the acidic solution over a defined product-dependent and process-dependent time. The entire contents of the bag therefore experience the inactivation with virtually identical detention time and consequently the virus reduction carried out is likewise virtually identical in each fluid element of the container.

If now a process for the production of biopharmaceutical and biological products, in particular pharmaceutical antibodies, is to be run in the continuous operating mode, then the holding time (=detention time) required would have to be effected for the virus inactivation.

Continuous virus inactivation, in the context of the application, means that the feed of the feed stream into the virus inactivation module and the removal of the product stream from the virus inactivation module proceed without pause.

A possibility for carrying out continuous virus inactivation is irradiation with UV-C light. WO2002038191, EP1339643B1, EP1464342B1, EP1914202A1 and EP1916224A1 describe the use of a helical detention loop in which the material that is to be inactivated is irradiated with UV-C light and the viruses present are consequently inactivated. If a fluid flows through a helically coiled tube, the centrifugal force acts on the fluid. These centrifugal forces induce secondary flows (what are termed Dean vortices), which leads to an improved radial throughflow and therefore more homogeneous irradiation of the material that is to be inactivated. The helix structure used in said sources is a straight helical coil without changes to the direction of the axes of the helix. For the application of a continuous virus inactivation at a low pH, the use of a straight helical structure, as is used in the UV-C irradiation, is not practicable, since, although the detention time distribution is narrower than in the straight tube with laminar throughflow, it is still too broad. Due to the still comparatively broad detention time distribution, this geometry would additionally require a large plant for pH virus inactivation.

In a laminar tube flow, a parabolic velocity profile forms, as a result of which a broad detention time distribution occurs (FIG. 1). Since the maximum velocity in the centre of the tube flow is twice the median velocity, but at the tube walls the velocity is equal to zero (adhesion condition), in these cases a very broad detention time distribution occurs. The resultant detention times are between half the average detention time (caused by the rapidly flowing fluid elements in the tube centre) and an infinitely long detention time (caused by the adhering fluid elements in the vicinity of the wall). Since, firstly, for effective inactivation of the viruses, a minimum detention time is required, and secondly, however, long detention times at a low pH could damage the product (such as, e.g., a protein), achieving a narrow detention time distribution in continuous operation is vital. A change from the laminar flow situation to a turbulent plug flow with uniform detention time, in this case, is not an acceptable alternative. Turbulent flows assume high flow velocities. If, then, the long detention times customary for virus inactivations at low pH (for example 60-120 min) are achieved, disadvantageously large plants are formed, which also have a high pressure drop.

WO1998/02237 describes a solution to the problem of the parabolic velocity profile in a continuously operated tubular reactor for precipitating products from a liquid reaction mixture by the application of a segmented procedure (Segmented Flow Processes), in which discrete volumes of the reaction mixture are separated from discrete volumes of a separating liquid which is immiscible with the reaction mixture, wherein the detention time of the reaction mixture in the tubular reactor is sufficient for the precipitation. The discrete volumes are generated under plug flow conditions and for each volume the reaction conditions are substantially identical, in such a manner that a uniform product is obtained for each volume.

Tuercke et al. describe the segmented conduction—liquid/liquid or liquid/gas—in microstructured reactors in continuous operation for the organic synthesis and production of microparticulate products such as, e.g., multiple emulsions and nano particles and polymerization (Organic Process Research & Development 2009, 13, 1007-1013). The method of the segmented phase was also used by the Fraunhofer Institute for Chemical Technology ICT for separating cells. The technique of segmented phases is, in addition, used in the sample transport in the Baychromat® System for sampling and analysis (US 2009/0178495).

The applicability of plug flow conditions or segmented flow for methods simultaneously require a long detention time and a narrow detention time distribution such as, e.g., virus inactivation at a low pH, has not to date been studied or mentioned.

SUMMARY

Proceeding from the prior art, the object was to provide a novel, simple and inexpensive solution which permits the required detention time in a detention time segment with continuous flowthrough for continuous virus inactivation, in particular at a low pH, with a narrow detention time distribution.

The invention achieves this object by a method for continuous virus inactivation of a product stream that is to be inactivated in a reactor 1 having a low hydraulic diameter of 0.01 mm to 6 mm, preferably 0.5 mm to 3 mm, comprising the following steps:
a) Provision of the product stream that is to be inactivated,
b) Setting the virus-inactivating conditions,
c) Introducing a separating medium that is immiscible with the product stream into the product stream to segment it,
d) Feed and passage through of the segmented product stream from c) under virus-inactivating conditions in a detention segment formed by the reactor 1,
e) Outflow from the detention segment,
f) Preferably continuously separating off the separating medium.

DETAILED DESCRIPTION OF A PREFERRED EMBODIMENT

Preferably the reactor, and also the elements of the module for segmenting the product stream that come into contact with the product stream, are sterilizable, preferably autoclavable, gamma-irradiatable or treatable with ethylene oxide (ETO) gas, which permits a low-microbe or even sterile operation.

Preferably, the reactor is a tubular reactor. Particularly preferably, a tubular reactor made of a disposable material, e.g. a flexible tube, is used, which is discarded after use in order to be able to dispense with cleaning. For this property, preferably a flexible tube is used which conforms to the relative quality requirements, e.g. medical quality (USP Class VI). For example, the tubular reactor is a flexible tube made of silicone. As examples, the flexible tubes Pharmed®-BPT (silicone flexible tube), C-Flex-374® (thermoplastic flexible tube), or Sanipure® from Saint-Gobain Performance Plastics may be mentioned, without restricting the invention thereto. In the test plant, a commercial flexible tube of SaniPure® having an internal diameter of 1.6 mm was used.

The geometric configuration in the length of the tubular reactor is as desired: straight, coiled or curved, provided that it does not snap off. Preference is given to a space-saving arrangement of the tubular reactor. Typically, the tubular reactor is supported by a support structure. For example, the tubular reactor is coiled around frames fastened one above the other on a stand, wherein the frames can be round or square. A helical coiling around one or more columns is also possible. For UV inactivation, the column can then have a UV lamp and the tubular reactor can be transparent to UV. Also, thermal virus-inactivating conditions via heating the support structure in the tubular reactor can be established. For thermal inactivation, the coiled structures can also be introduced into a liquid bath in order to induce steep temperature changes.

Alternatively, a tubular reactor can be used which is formed by one or more plates stacked one above the other, in particular plastic plates, in which a channel having an inlet and an outlet is incorporated. If this plate reactor comprises a plurality of plates, the inlet and the outlet of the centre plates are positioned in such a manner that a continuous channel of the desired length is formed by the stacks. Also, the geometric configuration in the length of the channel is as desired: straight, coiled or curved.

The cross section of the reactor 1 is typically round or oval, but can also be square.

In step a), a product stream of liquid is provided that can contain both product and also viruses that are potentially to be inactivated.

As possible virus-inactivating conditions for step b), a low pH (preferably ≤4), detergents, UV or thermal treatment are cited.

Figure 4:
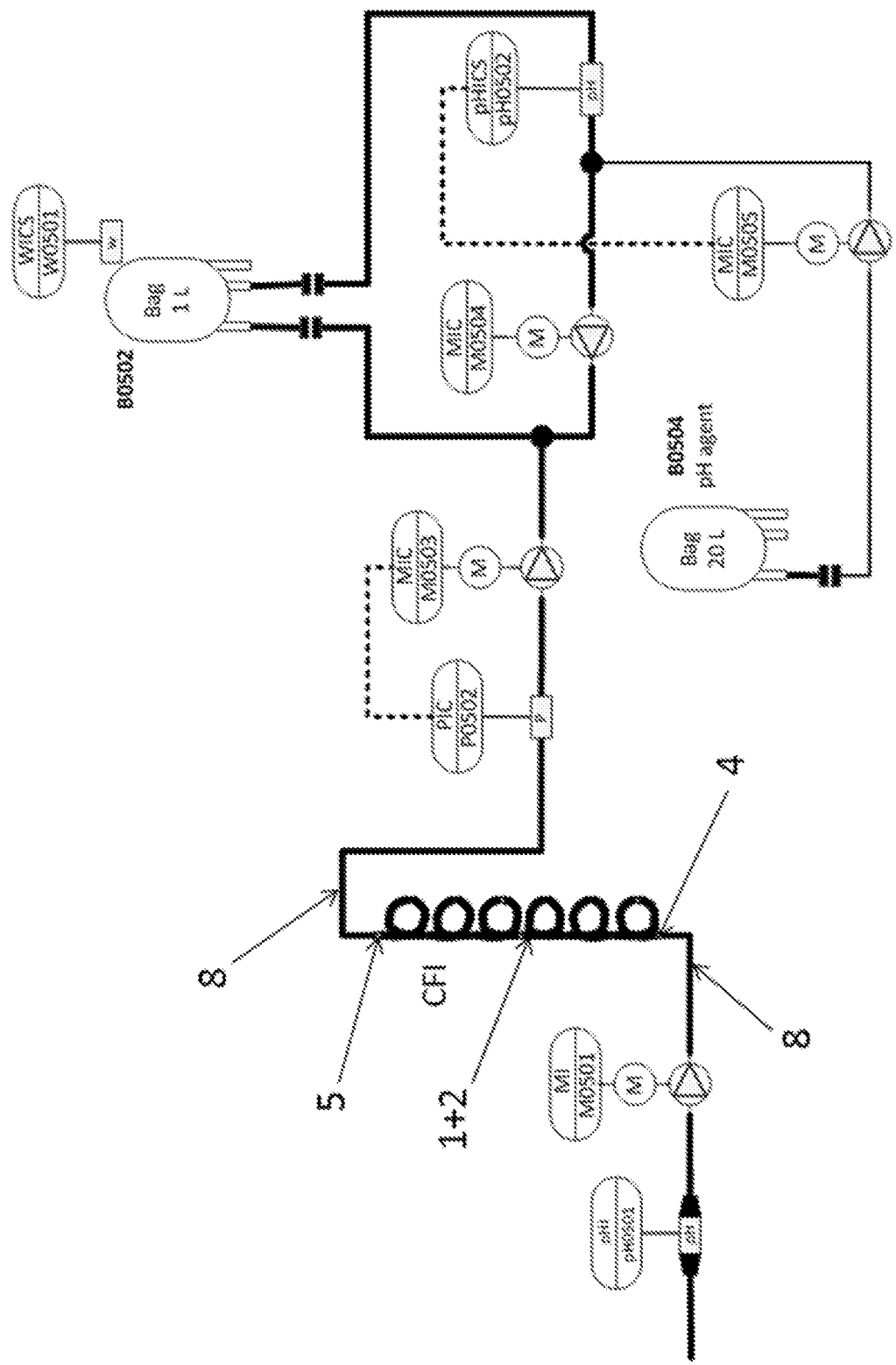

Preferably, in step b), the pH of the product stream is set to a pH≤4, provided that the pH of the material that is to be inactivated does not already have the required pH. The pH of the product stream is usually determined before entry into the device for virus inactivation by a sensor (FIG. 4). Usually, this pH sensor does not have control tasks. Recording the pH signal merely serves for process monitoring. Setting the pH of the solution that is to be inactivated to ≤4 can proceed, for example, by addition of HCl solution. The solution is typically added in the run-up of the device to virus inactivation. After step e) or f), usually the pH is set to >4 using a base, for example sodium hydroxide solution (NaOH), in order to terminate the virus inactivation. The neutralization can be carried out as a batch operation or as a continuous production method, and thus be integrated into a batch process or a continuous process.

As separating agent, in the method according to the invention, a phase that is immiscible with the product stream is used. Preferably, the separating agent is an oil or a gas such as, for example air, $CO_2$ or nitrogen, preferably a gas, particularly preferably nitrogen, owing to the reaction inertia thereof with respect to the product stream and low solubility in the aqueous product stream.

Figure 3:
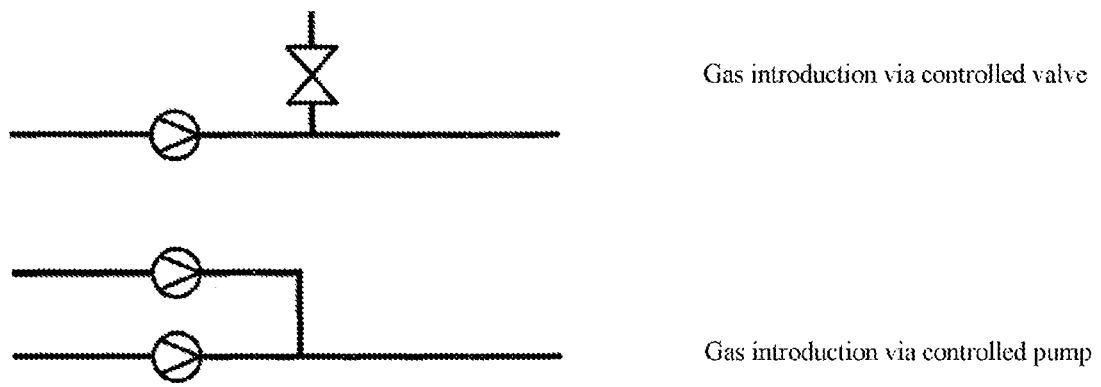

For introducing the separating agent and segmenting the product stream in step c), the reactor typically, in addition to an intake 4, has an intake 6 for the separating agent usually in the form of a T-piece, to which a means for introducing a pulse to the separating agent—either an actuated opening valve having an attached pressure line or a pump—is connected (FIG. 3). The segmentation proceeds, for example, with a pump having a pulse rate of 0.1 to 200 pulses per minute.

Usually, the reactor stream flows through at a volumetric flow rate from 1 to 1000l/min, preferably 10 to 100 ml/min.

As an alternative to pulsed introduction, the separating agent can be fed continuously via a membrane. In this embodiment, a module for segmenting the product stream is used that comprises one or more hollow fibres having a hydrophobic wall, through which the separating agent is introduced into the product stream. It is also possible to employ a hollow-fibre module having a hydrophilic wall, wherein in the lumen of the hollow fibres, the separating agent is continuously transported and introduced through the wall of the product stream. This second embodiment assumes that the pores of the hollow fibres are permeable to the product. The use of a membrane segmentation generally assumes that the virus-inactivating conditions do not impair the required properties of the membrane. When detergents are used, the employment of a T-piece is therefore preferred.

Chemical introduction of a separating agent, e.g. $CO_2$, would also be possible, in particular if the virus-inactivating conditions tolerate pH variations.

By such segmentations of the product stream, usually product stream volumes from 0.1 ml to 100 ml are formed with volume separations of 0.1 ml to 10 ml between two product stream volumes.

Usually, the minimum length of a segment, in particular of a separating agent segment is three times the internal diameter of the reactor. A reasonable maximum length of a segment is one fifth of the detention segment.

Owing to the capillary action and the surface tension in the reactor, the segmentation of the phases is maintained, in such a manner that two segments of one phase are separated by a segment of the other phase. As a result, back mixing between two segments of a phase is minimized and the detention time distribution of the overall system narrowed enormously.

The individually transported product stream segments (=product stream volumes) can be regarded as small inactivation containers that are always completely emptied and also mixed only minimally with one another.

Usually, the product stream in step d) is fed and transported to the reactor with a flow velocity of 0.1 to 1000, preferably 1 to 100, particularly preferably 10 to 100 ml/min, usually using a pump. In this step the desired contact time (=detention time) between the virus-inactivating conditions, in particular the acidic solution and any viruses present, proceeds. The detention time is sufficiently long in order to inactivate the viruses without damaging the product too greatly. It is usually determined experimentally in a batch method, before being converted to a continuous method, and is typically from 30 min for pH-sensitive products to 10 h for less sensitive products. The required detention time and also the maximum detention time are product-dependent. The maximum detention time is usually optimized in such a manner that the product is damaged minimally in order to keep the requirement for downstream purification steps as small as possible.

As design parameters for the method according to the invention there may be mentioned correspondingly:

Tube interior diameter di of the reactor

Tube length L, wherein the tube length L and inner diameter of the tube are adapted to the dimensions of the overall plant/throughflow rate of the plant in such a manner that the detention times required in the respective application case are met Desired volumetric flow rate, product stream volume, separating agent volume and pulse rate.

The separating agent is usually continuously separated off by a separator which acts via gravity, centrifugal force or by membrane properties.

If a gas is used as separating agent, the volume stream is usually continuously degassed. For this purpose, a bubble trap, a venting valve, or preferably a membrane degassing module can be used.

If the production process requires one or more adjustments of the pH, the device for virus inactivation is usually connected to a unit for adjusting the pH. Usually, two units for adjusting the pH are used, the first upstream of the inactivation for adjusting the product stream to a pH≤4, a further downstream of the inactivation for neutralizing the product stream.

If the device for virus inactivation is integrated into a continuous production process, one or more units for adjusting the pH are preferred, in which the product stream flows through a recirculation loop. FIG. 4 depicts the virus inactivation and a subsequent neutralization by way of example, without being limited thereto. M0503 transports the product stream to the bag B0502 where the pH is adjusted after it leaves the virus inactivation to pH≥4. The recirculation pump M0504 transports the contents of the bag B0502 through the recirculation loop in which the pH sensor pH0502 measures the pH of the product stream. Downstream of the sensor pH 0502, the adjusting agent for adapting the pH is added to control the pH. This proceeds via the default setting of the speed of rotation for M0505.

In the method according to the invention, the product stream that is to be inactivated is usually a solution from a bioreactor or a chromatography column, in particular a protein or peptide solution such as, e.g., an antibody solution.

The technical advantage of the continuous virus inactivation according to the invention compared with the virus inactivation in the batch mode that is conventional in the prior art is in its ability to be integrated into a continuous work-up process, also termed "downstream processing", without needing to change the process procedure. In this case, there is no change in the process procedure from batch to continuous and back again, but the entire downstream processing, or optionally the entire production process (upstream and downstream) can be run through continuously. Also, continuous virus inactivation can more readily be combined with a continuous sub-step of an otherwise batchwise work-up process.

The present invention including preferred embodiments is explained in combination with the drawings and examples hereinafter, without being restricted thereto. The embodiments can be combined as desired with one another, provided that the opposite does not clearly result from the context.

Figure 1:
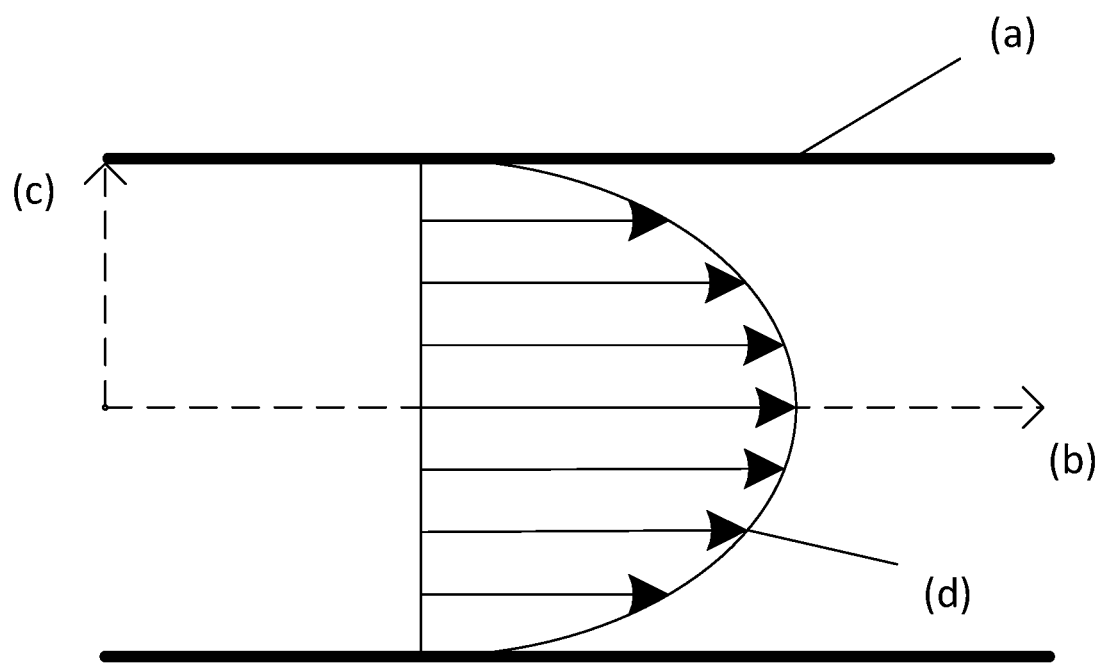
FIGS. 1-6 depict embodiments of the present disclosure.
Figure 1:
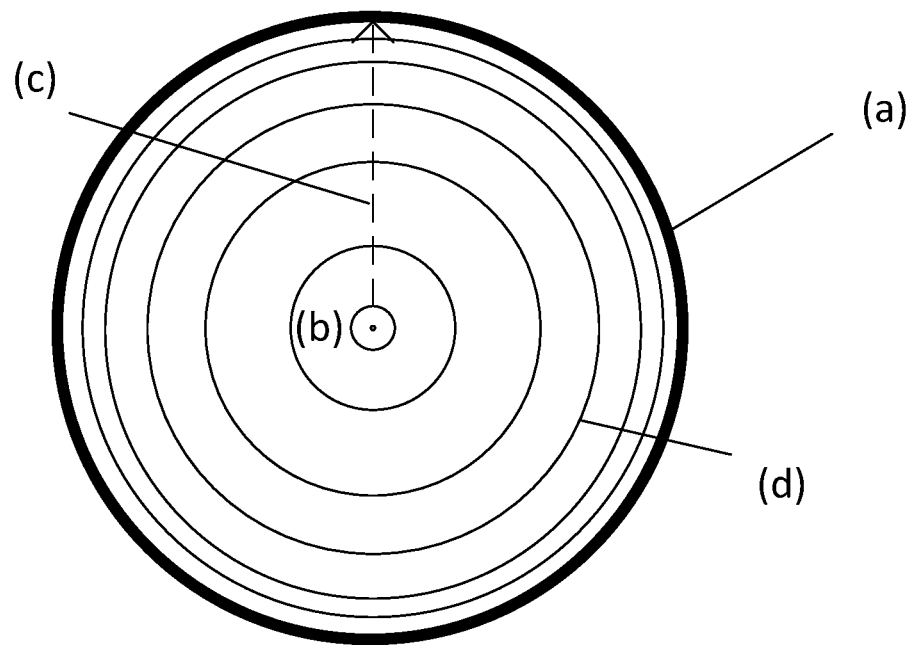

The reference signs used are:

1=Curved and/or helically coiled tube or flexible tube
2=Direction reversal and/or bend 2 of the coil axis h having an angle α of 45° to 180°
3=Frame
4=Inlet
5=Outlet
6=Holding stand
7=Foot
8=Product flow line FIG. 1 shows a parabolic flow profile of the tube with laminar throughflow (top: longitudinal section of the tube). Lines of equal velocity in the direction of flow in the tube with laminar throughflow (bottom: cross section of the tube).

a=Tube wall
b=Axial direction of the tube in the direction of flow
c=Radial direction
d=Lines of equal flow velocity in the direction of flow.

Figure 2:
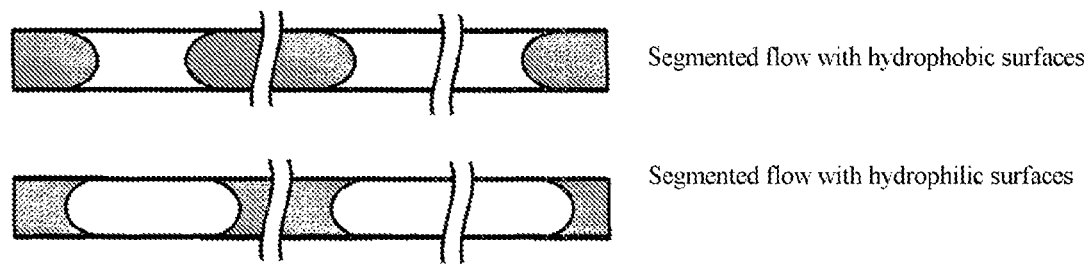

FIG. 2 shows the principle of segmentation.

FIG. 3 shows alternative means for pulsed introduction of the separating agent connected to the tubular reactor.

FIG. 4 shows a flow chart of the virus inactivation with subsequent adaptation of the pH, wherein the device for virus inactivation is shown only schematically.

Figure 5:
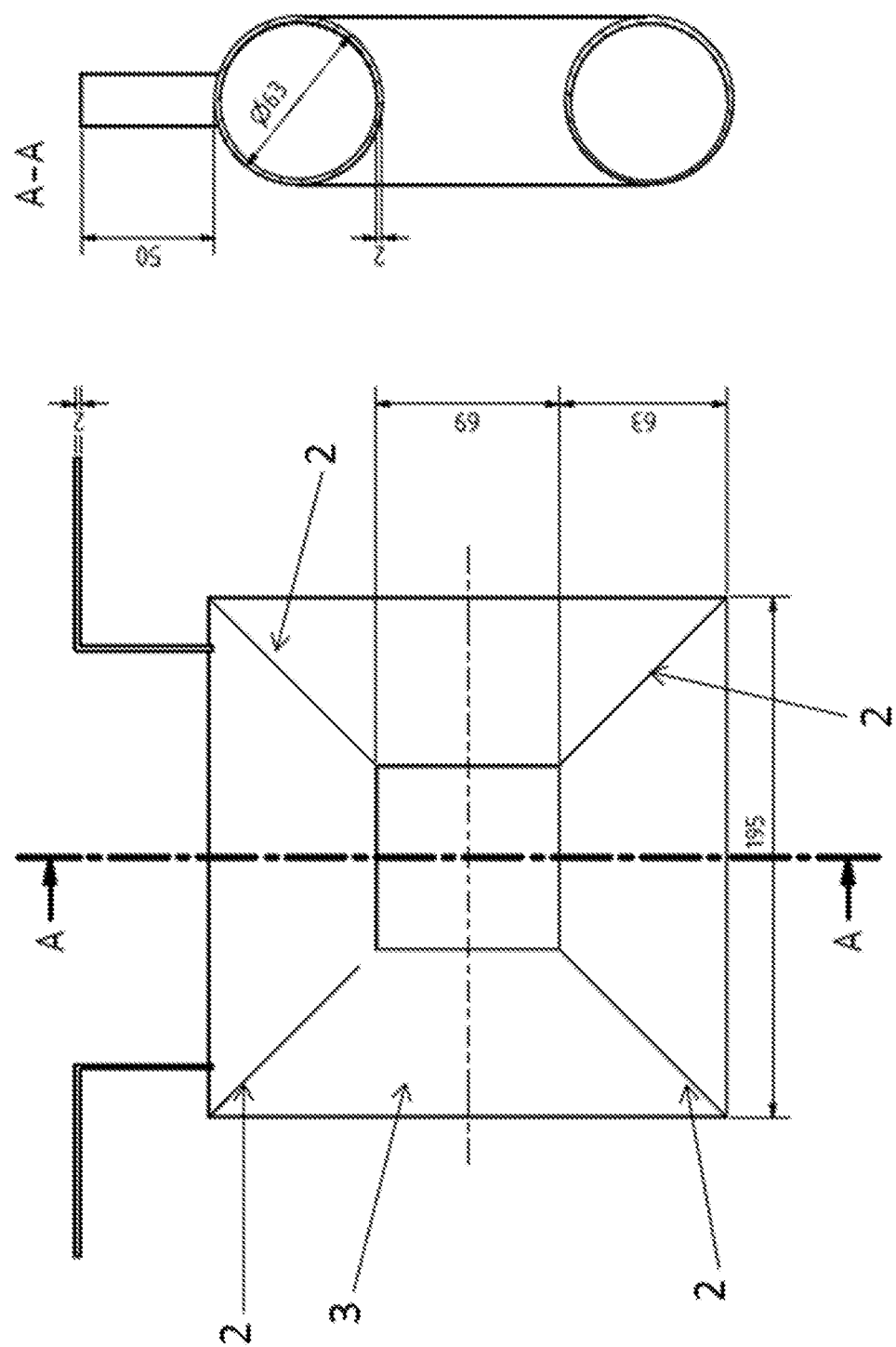

FIG. 5 shows a square frame for coiling the reactor tube.

Figure 6:
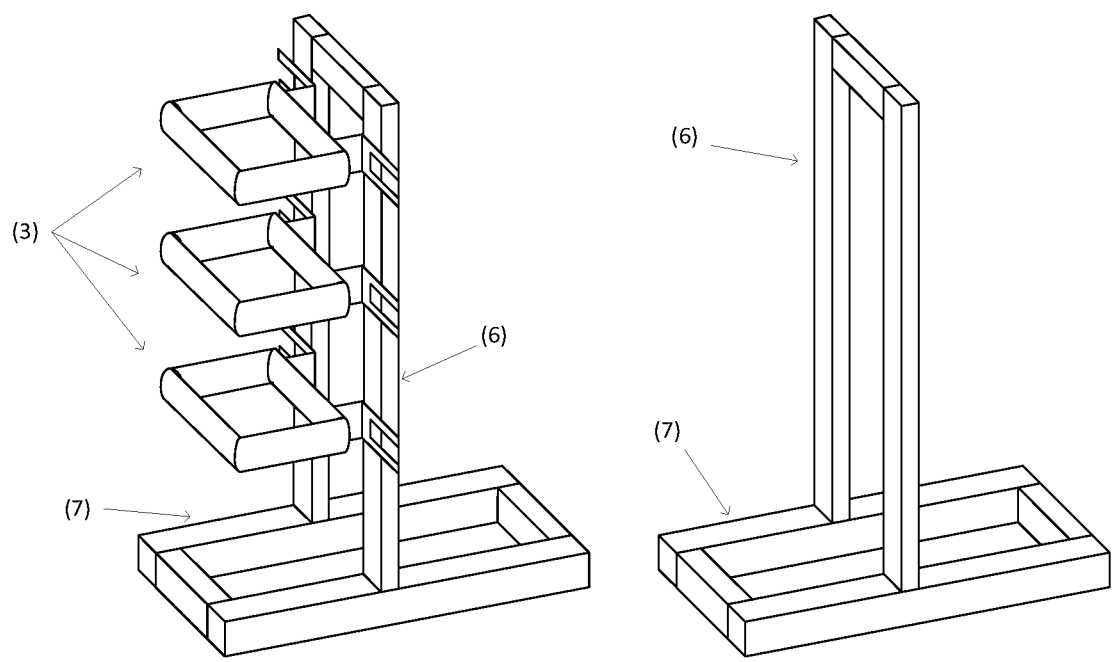

FIG. 6 shows a plurality of frames mounted on a stand.

Example 1

For the experimental studies, a flexible tube internal diameter of 1.6 mm was selected. The tubular reactor was wound onto frames having the following dimensions—frame diameter of 63 mm; outer edge length of the frame 195 mm. The frame was fabricated in accordance with FIG. 5, and mounted on a stand according to FIG. 6.

In each case 11 coils having a minimum separation were carried out per arm. The flexible tube length used per frame is in proportion to the frame diameter with the assumption of constant number of coils per arm.

In this case, the exit of the upper frame was connected to the entry of the frame beneath it in such a manner that the flexible tube coiling of the frame ran from top to bottom. Alternatively, it is also possible for the flow to flow from bottom to top or in the horizontal.

A volumetric flow rate of around 3 ml/min flowed through the test plant.

The experiments for detention time measurement in the device for continuous virus inactivation were carried out using a UV measurement at the outlet of the system.

The tracer substance used was a vitamin B12 solution having a concentration of 0.25 g/l, since vitamin B12 absorbs UV light at a wavelength of 280 nm and therefore is suitable as an indicator.

First, the device was purged with distilled water. At time point k, at the inlet of the virus inactivation the system was switched over to the tracer solution and the recording of the measurement signal of the UV sensor was started (consequently a step function of the tracer solution was applied to the system). When the UV signal at the outlet of the system corresponded to the UV signal of the tracer solution, the experiments could be terminated, since the system, from this time point, was completely filled with tracer solution and therefore the response of the system to the step function was completely recorded.

The work which led to this application was funded under financial aid agreement "Bio.NRW: MoBiDiK—Modular bioproduction—disposable and continuous" in the scope of the European Fund for Regional Development (EFRD).

The invention claimed is:

1. A method for continuous virus inactivation of a product stream that is to be inactivated in a reactor having a low hydraulic diameter of 0.01 mm to 6 mm, comprising:
   a. providing a product stream that is to be inactivated,
   b. setting a virus-inactivating condition, wherein the virus-inactivating condition comprises a low pH, using a detergent, or UV or thermal treatment,
   c. introducing a separating medium that is immiscible with the product stream into the product stream to segment the product stream,
   d. feeding and passaging the segmented product stream from c) under the virus-inactivating condition through a detention segment formed by the reactor,
   e. outflowing the segmented product stream from the detention segment.

2. A method according to claim 1, wherein, in b), the pH of the product stream is set to ≤4, provided that the pH of the product stream that is to be inactivated does not already have the required set pH.

3. A method according to claim 1, wherein the product stream that is to be inactivated is a solution of macromolecules.

4. A method according to claim 1, further comprising a step f), wherein, in f), the separating medium is separated off continuously.

5. A method according to claim 1, wherein the reactor has a hydraulic diameter of 0.5 mm to 3 mm.

6. A method according to claim 1, wherein the product stream that is to be inactivated is a protein or peptide solution.

7. A method according to claim 1, wherein the product stream that is to be inactivated is an antibody solution.

8. A method according to claim 1, wherein the virus-inactivating condition is a low pH of ≤4.

9. A method according to claim 1, wherein the virus-inactivating condition is using a detergent.

10. A method according to claim 1, wherein the virus-inactivating condition is UV or thermal treatment.

\* \* \* \* \*